US006867196B1

(12) United States Patent
Wolff et al.

(10) Patent No.: US 6,867,196 B1
(45) Date of Patent: Mar. 15, 2005

(54) PROCESS FOR DELIVERING NUCLEIC ACIDS TO CARDIAC TISSUE

(75) Inventors: Jon A. Wolff, Madison, WI (US); Hans Herweijer, Madison, WI (US); Larry F. Whitesell, Lodi, WI (US); Matthew R. Wolff, Middleton, WI (US); Sean D. Monahan, Madison, WI (US); Paul M. Slattum, Madison, WI (US); James E. Hagstrom, Middleton, WI (US); Vladimir G. Budker, Middleton, WI (US); David B. Rozema, Madison, WI (US)

(73) Assignee: Mirus Bio Corporation, Madison, WI (US)

(*) Notice: Subject to any disclaimer, the term of this patent is extended or adjusted under 35 U.S.C. 154(b) by 0 days.

(21) Appl. No.: 09/330,909

(22) Filed: Jun. 11, 1999

Related U.S. Application Data

(63) Continuation-in-part of application No. 09/447,966, filed on Nov. 23, 1999, now Pat. No. 6,627,616, which is a continuation-in-part of application No. 09/391,260, filed on Sep. 7, 1999, which is a division of application No. 08/975,573, filed on Nov. 21, 1997, now Pat. No. 6,265,387, which is a continuation of application No. 08/571,536, filed on Dec. 13, 1995, now abandoned.

(60) Provisional application No. 60/100,168, filed on Sep. 14, 1998.

(51) Int. Cl.[7] .......................... A61K 31/70; A01N 43/04
(52) U.S. Cl. ........................................................ 514/44
(58) Field of Search .................... 424/93.21; 514/44; 435/115

(56) References Cited

U.S. PATENT DOCUMENTS

| | | | |
|---|---|---|---|
| 5,674,192 A | * 10/1997 | Sahatjian et al. | 604/28 |
| 5,693,622 A | * 12/1997 | Wolff et al. | 514/44 |
| 5,698,531 A | 12/1997 | Nabel et al. | 514/44 |
| 5,792,453 A | 8/1998 | Hammond et al. | 424/93 |
| 5,830,879 A | * 11/1998 | Isner | 514/44 |
| 5,922,687 A | * 7/1999 | Man et al. | 514/44 |
| 6,627,616 B2 | * 9/2003 | Monahan et al. | 514/44 |

OTHER PUBLICATIONS

Hajjar, R.J. et al. Proc. Natl. Acad. Sci. USA 95;5251–5256, Apr. 1998.*
Leclerc, G et al. J. Clin. Invest. 90:936–944, Sep. 1992.*
Anderson, W.F. Nature 93:25–30, Apr. 1998.*
Verma, I. M. et al. Nature 389:239–242, Sep. 1997.*
Morishita, R. et al. J. Clin. Invest. 91:2580–2585, Jun. 1993.*
Merriam–Webster's Medical Desk Dictionary; Merriam–Webster Inc., Springfield, MA, 1993.*
Acsadi, G. et al., "Direct Gene Transfer and Expression Into Rat Heart In Vivo." *The New Biologist* Jan. 1991; vol. 3, No. 1; 71–81.
Barr, E. et al., "Efficient Catheter–Mediated Gene Transfer Into the Heart Using Replication–Defective Adenovirus." *Gene Therapy* 1994; 1; 51–58.
Lin, H. et al., "Expression of Recombinant Genes in Myocardium In Vivo After Direct Injection of DNA." *Circulation* Dec. 1990; vol. 82, No. 6; 2217–2221.
Losordo, D. et al., "Gene Therapy for Myocardial Angiogenesis." *Circulation* 1998; 98; 2800–2804.
Mack, C. et al., "Salvage Angiogenesis Induced by Adenovirus–Mediated Gene Transfer of Vascular Endothelial Growth Factor Protects Against Ischemic Vascular Occlusion." *Journal of Vascular Surgery* Apr. 1998; vol. 27. No. 4; 1–12.
Donahue, JK. et al., "Acceleration of Widespread Adenoviral Gene Transfer to Intact Rabbit Hearts by Coronary Perfusion With Low Calcium and Serotonin." *Gene Therapy* 1998; vol. 5; 630–634.
Gal, Dov et al., "Direct Myocardial Transfection In Two Animal Models," *Laboratory Investigation* 1993; vol. 68, No. 1; p. 18.
Hajjar, Roger J. et al., "Modulation of Ventricular Function Through Gene Transfer In Vivo," *Proc. Natl. Acad. Sci. USA* Apr. 1998; vol. 95, pp. 5251–5256.

* cited by examiner

Primary Examiner—Joe Woitach
(74) Attorney, Agent, or Firm—Mark K. Johnson

(57) ABSTRACT

A process for delivering a nucleic acid to a cardiac tissue cell in a mammal is described, comprising introducing a composition consisting of a nucleic acid to a blood vessel, which subsequently delivers the nucleic acid to the cardiac tissue cell. The nucleic acid can be DNA or RNA or plasmid DNA or viral. This process is for purposes of gene therapy, and research.

10 Claims, 5 Drawing Sheets

PROCESS FOR DELIVERING NUCLEIC ACIDS TO CARDIAC TISSUE

This application claims benefit to provisional application 60/100,168 filed on Sep. 14, 1998 and is a continuation-in-part of application Ser. No. 09/447,966, filed on Nov. 23, 1999, now U.S. Pat. No. 6,627,616, which is a continuation-in-part of application Ser. No. 09/391,260, filed on Sep. 7, 1999, which is a division of application Ser. No. 08/975,573, filed on Nov. 21, 1997, now U.S. Pat. No. 6,265,387, which is a continuation of application Ser. No. 08/571,536, filed on Dec. 13, 1995, now abandoned.

FEDERALLY SPONSORED RESEARCH

This invention was made with United States government support from NIH Grant Number DK49117. The United States has certain rights in this invention.

FIELD OF THE INVENTION

The invention generally relates to techniques for delivering nucleic acids to a heart for purposes of gene therapy. More particularly, the invention involves vascular delivery of DNA and RNA to a heart for gene expression or gene regulation.

BACKGROUND

Gene therapy is an approach to treating diseases based on the expression of genes toward a therapeutic goal. Gene therapy has been discussed in the context of treating diseases although it also has a potential for disease prevention.

A basic challenge in gene therapy is to develop approaches for delivering genetic material to the appropriate cells of a patient in a way that is specific, efficient and safe. This problem of "drug delivery," where the gene is a drug, is particularly challenging. If genes are appropriately delivered they can potentially lead to a cure. A primary focus of gene therapy is based on strategies for delivering genes.

Gene therapy promises to be a singular advance in the treatment of both acquired and genetic diseases at the most fundamental levels of pathology. Specifically, the development of gene transfer methods into the heart is attractive given that coronary artery disease is the leading cause of morbidity and mortality in the United States. Despite advances in the prevention and treatment of this disorder there remains a large population of patients who are not optimal candidates for percutaneous or surgical revascularization, usually because of severe distal vessel disease or previous failed revascularization procedures. Coronary collateral development is an important adaptive response of the ischemic heart in this situation, but often the collateral circulation is inadequate and results in severe angina pectoris despite maximal medical therapy. A new strategy to treat these often disabled patients involves the local delivery of vascular cytokines to induce new blood vessel growth (neoangiogenesis) in the ischemic myocardium. It has been recognized that gene therapy could play a major role in neovascularizarion approaches.

A variety of techniques has been developed to transfer genes into the heart. They have principally involved adenovirus vectors, which can be injected directly or intravenously, and plasmid DNA vectors injected directly into the heart tissue. The first reports of successful non-viral in vivo gene delivery to the heart used direct injection of plasmid DNA vectors (H. Lin, M. S. Parmacek, G. Morle, S. Bolling and J. M. Leiden. Circulation 82:2217–2221, 1990; G. Acsadi, S. S. Jiao, A. Jani, D. Duke, P. Williams, W. Chong and J. A. Wolff, New Biologist 3:71–81, 1991). High levels of $\beta$-galactosidase reporter gene expression were measured several days after injection of plasmid DNA solutions. Expression appeared to be highly localized to the site of injection. $\beta$-Galactosidase expression in the heart was not stable, apparently as the result of a host immune response against the expressing cells. Adenoviral vectors have been used extensively for gene transfer into cardiac muscle. Barr et al., found transduction levels of 10–32% after intracoronary installation. However, expression was also found in endothelial cells and the presence of the viral genome was detected in other organs (E. Barr, J. Carroll, A. M. Kalynych, S. K. Tripathy, K. Kozarsky, J. M. Wilson and J. M. Leiden. Gene Therapy 1:51–58, 1994). Many of these gene therapy studies were aimed at transducing vascular endothelial cells to prevent restenosis following angioplasty. The injection of adenoviral vectors into the portal or systemic circulatory systems leads to high levels of foreign gene expression in several organs (liver, lung, etc.) that is transient. As has been observed after adenovirus transduction of transgenes into other organs, expression in the heart is also transient. Immune responses directed against the viral coat proteins, proteins expressed from the viral genome, and the expressed transgene all contribute to the rapid elimination of transduced cells. Adenoviral transduction of infarcted heart tissue is less efficient than normal tissue. This could be a problem for viral gene therapy approaches for ischemic heart disease.

Until recently, the direct injection of plasmid DNA into the heart has mainly been used to benefit basic researchers investigating transcriptional regulation of cardiac specific genes. Isner and co-workers have pioneered the in vivo delivery of genes that result in neovascularization of ischemic muscle. In a breakthrough gene therapy study, they demonstrated significant formation of new vessels, enhanced distal flow, and clinical benefit in patients with ischemic limbs following injection of plasmid DNA expressing the human vascular endothelial growth factor (hVEGF) gene. This same hVEGF-expressing plasmid has recently been injected into ischemic heart tissue in humans. Preliminary results are very promising, with significant reduction in reported angina, and improved Rentrop score in 5 of 5 patients.

In vivo transfection of plasmid DNA complexed with liposomes after direct injection into heart muscle resulted in localized expression of reporter genes. While highly effective in vitro, liposome-complexed plasmid DNA particles generally have been of limited success in vivo. Other methods have involved the systemic delivery of adenoviral vectors or liposome-plasmid DNA complexes (e.g., injection into the tail vein of mice). Following systemic delivery, gene transfer into liver and lung is much more efficient than into heart, making this strategy unattractive for human cardiac gene therapy.

Vascular endothelial growth factor (VEGF) and various isoforms of fibroblast growth factor (FGF) are mitogens of endothelial and vascular smooth muscle growth in vitro and have been shown to induce neoangiogensis and ameliorate ischemia in animal models of vascular occlusion. In the rabbit hindlimb ischemia model, angiogenesis and increased collateralization have been demonstrated following intravenous, intra-arterial, and intramuscular injections of recombinant human VEGF. Similar effects of VEGF have been demonstrated in the coronary circulation. Banai and colleagues demonstrated that direct intracoronary injections of hVEGF (45 $\mu$g/d, 5 d/week×4 weeks) into an occluded coronary artery increased capillary density and improved coronary blood flow in a dog coronary occlusion model. Unfortunately, systemic arterial injections of VEGF did not improve collateral blood flow in the same model. Fibroblast growth factor likely has similar effects. Basic fibroblast growth factor has been shown to increase collateral blood flow in rat and rabbit hindlimb ischemia models. Repeated intracoronary and intra-arterial injections of basic fibroblast growth factor increased collateral circulation in the canine chronic coronary occlusion model. However, intravenous infusions of basic FGF protein are not efficacious in improving collateral coronary circulation in this model. While both VEGF or FGF induce neoangiogenesis and ameliorate ischemia in animal models of vascular occlusion, this strategy is clearly limited by the need for repetitive direct intra-arterial or intramuscular injections of the recombinant protein. In addition, the recombinant protein can cause significant systemic side-effects when administered in effective doses. An alternative strategy involves the use of sustained-release polymer to deliver cytokines locally to ischemic myocardium, but surgical implantation of these polymers is required. The difficulty and expense associated with large-scale recombinant protein manufacture is another limitation for potential clinical use of this strategy.

Local delivery of VEGF or FGF to ischemic muscle has also been achieved by gene transfer of complimentary deoxyribonucleic acid (cDNA) for these proteins via arterial infusion or direct needle injection of plasmid DNA. Direct intramuscular injection and percutaneous intraarterial injection of a human VEGF plasmid DNA expression vector induces collateral vessel development in the rabbit hindlimb ischemia model. Using the same model, it was demonstrated that intra-arterial injection of plasmids expressing either of three isoforms of human VEGF (hVEGF$_{121}$, hVEGF$_{165}$, and hVEGF$_{189}$) are equally efficacious in inducing collateral vessel growth.

Using a porcine chronic coronary occlusion model, it was shown that single coronary injections of a replication-defective adenovirus vector expressing fibroblast growth factor-5 (FGF-5) resulted in improved regional myocardial blood flow and histologic evidence of increased capillary number. Stress-induced regional contractile dysfunction was documented by echocardiography after coronary occlusions in this study. Importantly, this pacing-induced regional wall motion abnormality was completely normalized within two weeks after intracoronary FGF-5 gene transfer and the amelioration of stress-induced myocardial ischemia persisted for at least 12 weeks. Again using the porcine model chronic coronary occlusion model, Mack et al. showed similar amelioration of pacing-induced myocardial ischemia and improvement in blood flow after multiple direct intramyocardial injections of a replication-defective adenovirus expressing hVEGF$_{121}$.

Despite these limitations, the feasibility of these approaches to treating human vascular ischemic diseases has recently been demonstrated in two preliminary studies. Jeffrey Isner's group at St. Elizabeth's Medical Center in Boston recently reported encouraging preliminary results following intramuscular injection of naked plasmid DNA encoding hVEGF$_{165}$ into the ischemic limb of patients suffering from severe peripherial vascular disease. Lower extremity perfusion (as measured by the ankle-brachial index) was improved in 7 of 10 treated patients.

In addition, improvement was noted in 4 of 7 patients with non-healing ischemic ulcers. Side effects were limited to lower extremity edema in 6 of the 10 treated patients. Neoangiogenesis in ischemic myocardium also showed clinical promise. Schumacher et al. injected recombinant basic fibroblast growth factor into myocardium surrounding the anastomosis of the internal mammary graft to the left anterior descending coronary artery in 20 patients undergoing coronary artery bypass surgery. Digital subtraction angiography demonstrated new capillary growth in the area of the injection.

SUMMARY

Non-viral versus Viral Vectors

Non-viral vectors have several advantages over viral vectors. Although in some situations non-viral vectors do not efficiently transfect target cells, under the right conditions their efficiency can be as high as for viral vectors. Especially the intravascular delivery of plasmid DNA was shown to be highly effective for gene transfer into liver, skeletal and cardiac muscle. Non-viral vectors are inherently safer than viral vectors, significantly lowering the cost of production, biosafety controls, and administration. A much lower risk of transforming activity is associated with plasmid DNA than the integrating viruses; plasmid DNA remains extrachromosomal in muscle tissue. A major problem associated with adenoviral vectors is the transient nature of expression. This is mostly related to an immune response directed against the transfected transgene and viral genes present in the vector. The anti-vector immune response may prevent repeat treatment with the same vector. Recent developments of "gutted" vectors devoid of viral genes, may diminish an immune response. However, there are still concerns regarding contaminating wild type viruses required for production of these novel vectors. Moreover, the capsid proteins in the viral particle can elicit an immune response, especially since most individuals will have been infected with several adenovirus strains during their lifetime.

The short duration of expression following adenoviral gene transfer is by itself not a disadvantage for neoangiogenesis gene therapy. Expression of hVEGF or hFGF should not be prolonged beyond the time indicated for therapeutic effect. We anticipate that expression levels from plasmid DNA vectors in the heart will also drop rapidly after 1–2 weeks. This is based on our observation that high expression levels in skeletal muscle drop significantly after the first two weeks and the experience with direct injection of plasmid DNA into cardiac muscle. However, the loss of expression from plasmid DNA vectors is related to an immune response directed against the expressed transgene or transcriptional shut-off, not to an immune response directed against the vector itself (see below) as is the case for adenovirus vectors.

Adenoviral transduction of infarcted heart tissue is less efficient than normal tissue. This is the opposite for plasmid DNA. Therefore, plasmid DNA vectors allow for more optimal targeting of the area of interest. The VEGF gene is currently considered the best candidate for induction of neovascularization. Expression of VEGF is strongly induced by hypoxia. Elements in the 3' untranslated region of the VEGF gene result in increased stability of the mRNA (ca. 2.5-fold). Therefore, plasmid DNA transfection can result in higher expression levels than adenovirus transduction, by targeting hypoxic cells.

Adenoviral vectors efficiently transduce not only cardiac muscle cells, but also endothelial cells when injected intravascular. This may be beneficial in some situations (e.g., prevention of restenosis), but is unwanted for many heart gene therapy applications. Promiscuous angiogenesis is especially significant as many patients with refractory ischemic heart disease also suffer from diabetes mellitus and exacerbation of diabetic proliferative retinopathy is a potential concern. Production of large quantities of adenovirus vector for clinical use is difficult, and repeated gene transfer is not possible due to the antigenicity of the adenovirus vector. The transduction of distant organs after intravascular adenovirus delivery is a major safety concern. This is much less of a risk for intravascular plasmid DNA delivery, since elevated pressure is required for efficient transfection.

Mechanism of Intravascular Delivery of plasmid DNA

Intravascular delivery into rat skeletal muscle results in efficient transfection of all muscle groups in the lower limb. In these experiments, 10 ml of plasmid DNA solution (50 $\mu$g plasmid DNA per ml saline) is injected into the external iliac artery, while clamping the external iliac vein, the internal iliac, the caudal epigastric, and the deferent duct arteries and veins. Up to 21% of all muscle fibers expressed $\beta$-galactosidase after pCI-LacZ injection. It was concluded that the intra-arterial pressure during the injection was a factor in transfection efficiency. For gene transfer into limb skeletal muscle, only arterial injections can be performed due to the presence of valves in the veins. Intravenous injection of plasmid DNA can be performed for gene delivery to the liver and to the heart, since the hepatic and coronary vasculature lack valves.

There is not much known about the mechanism of gene transfer following intravascular delivery of plasmid DNA. Blood vessels have a large number of small pores (~4 nm diameter) and only few large pores (~20–30 nm). The gyration radius for plasmid DNA molecules is in the order of ~100 nm. Yet, supercoiled plasmid DNA in plectonomic form has superhelix dimensions of approximately 10 nm. This implies that plasmid DNA is capable of crossing microvascular walls by stringing through the large pores. Pressure may be one method for transfection of liver and skeletal muscle and may enhance plasmid DNA transfer by opening the endothelial barrier. Raising the intravascular hydrostatic pressure transiently increases water flow through the large pores and thereby forces the extravasation of plasmid DNA. In the heart, plasmid DNA transfection following intravenous injection without temporary occlusion of the corresponding artery appears to be efficient. It seems that the microcapillary bed generates sufficient resistance to elevate intraluminal pressure to enable plasmid DNA extravasation.

Gene transfer into hepatocytes was increased by raising the osmolarity of the intraportal injection solution. This suggests that an increased osmotic pressure is one method to help extravasation of plasmid DNA, maybe through the destruction of tight junctions or increase of pore size following the osmotic shock to the endothelial cells. We suggest that the rate of plasmid DNA extravasation can be increased by enhancing fluid convection through the large pores by raising the transmural pressure difference in selective regions. This can be achieved by pressure injections (large volume, high injection rate), increased osmotic pressure, or addition of vasoconstrictors (lowering the volume of the injected bed). Vasodilators may increase plasmid DNA transfer by enhancing fluid and macromolecule leakage. Compounds that specifically act upon endothelial transport are of great interest. For instance, VEGF in high doses significantly enhances fluid leakage, probably by enlarging pore size. This is a rapid, transient process and appears non-toxic and the VEGF protein is rapidly degraded.

The use of intravascular naked plasmid DNA delivery to the heart provides an improved approach for in vivo cardiac gene therapy. This approach has several advantages over other methods: large genomic elements can easily be incorporated into plasmid DNA constructs.

Plasmids up to ~35-kb in size can be prepared and transfected, thus allowing for improved gene regulation. Plasmid DNA avoids immune responses directed against the vector or vector-expressed proteins.

Plasmid DNA vectors can be efficiently transfected into skeletal muscle cells in vivo via intravascular delivery under pressure. Up to 21% of all muscle cells in rat hind limbs express $\beta$-galactosidase after injection of 500 $\mu$g pCI-LacZ in 10 ml saline into the iliac artery. Similar experiments in pig heart demonstrated that cardiac tissue could be efficiently transfected following injection of 1.5 mg plasmid DNA in 30 ml saline. Transfection efficiency (as determined by luciferase expression) appeared equally efficient following injection into coronary arteries or veins. Most importantly, a retrograde approach, in which the plasmid DNA was delivered to heart muscle cells from the coronary vein, was as efficient as injection through the arteries. This indicates that this gene therapy approach would be useful in patients with occluded coronary arteries. Moreover, catheters advanced in coronary arteries may loosen and dislodge plaques, thus potentially causing occlusions.

In the heart, it appears that deterring free blood flow through the corresponding artery is not necessary for efficient gene transfer while delivering plasmid DNA through a coronary vein. It may very well be that the microcapillary bed allows efficient delivery. It is well known that the postcapillary venous endothelium allows the highest rates of fluid and macromolecule transport. In ischemic heart, blocked arteries may help to increase the pressure and thus gene transfer. In one preferred embodiment we intend to develop a clinically attractive methodology, we plan to deliver the plasmid DNA via a catheter. Balloon catheters can effectively define the bed size block the vein or artery behind the plasmid DNA delivery site.

Optimizing reporter gene expression and minimizing toxicity

For intravascular gene delivery into rat skeletal muscle, a predetermined volume in a predetermined period of time appears to be important to achieve high expression levels. The hypothesis is that high intravascular a predetermined volume in a predetermined period of time is required to initiate flow through the pores. The coronary vasculature in the circumflex is anatomically not identical from individual to individual. Moreover, a single bed (defined as artery into microcapillary bed into vein) may be connected to other beds (collateral flow), which can make it more difficult to obtain high pressure during injection. However, our experiments demonstrate that efficient gene transfer can be obtained by injection of plasmid DNA solutions into the vein (or artery), without preventing blood flow through the corresponding artery (or vein).

The target bed size in the heart will vary from case to case. In order to correlate variations in the injection parameters with expression, determination of the bed size is important. This can be done by injection of iodinated contrast detected by fluoroscopy. By performing this procedure prior to each plasmid DNA injection, gene transfer efficiency is expressed per total target bed size. It also allows for prediction of the required injection volume and speed. In one preferred embodiment (i.e., plasmid DNA extravasation and myocyte transfection), a threshold volume in a set time is exceeded and then maintained for a short time. This will form a square wave form on a plot of intravenous volume versus time. To reach the threshold, a larger injection volume or higher injection speed is required for a larger target bed. Therefore, an automatic injection system can be used to inject the plasmid DNA solution until this pressure threshold is reached and then maintain at or above this threshold for a given time. By creating a feedback between the intravenous pressure at the site of injection and the injection pump, a system can be created that automatically senses the target bed size and inject the proper amount of transfection solution. By limiting the injection volume per time unit, minimal tissue damage is incurred. All of the pigs injected recovered well from the procedure, and little damage was observed. Tissue sections from the injection site and stained with hematoxylin-eosin did not show any major histological abnormalities.

In a preferred embodiment, a process is described for delivering a nucleic acid to a cardiac tissue cell in a mammal, comprising: introducing a nucleic acid into a vessel; and, delivering the nucleic acid to the cardiac tissue cell.

In another preferred embodiment, a process is described for gene therapy, comprising: inserting a nucleic acid into a vessel having a channel leading to cardiac tissue; delivering the nucleic acid to a cardiac tissue cell; and, expressing the nucleic acid.

Reference is now made in detail to the preferred embodiments of the invention, examples of which are illustrated in the accompanying drawings.

A single balloon catheter generally comprises a two-lumen catheter, in which one lumen is used to inflate or deflate the balloon and the other lumen for other purposes, e.g., guidewires, delivery of fluids, intravascular pressure measurements. Such catheters are available in many different sizes (diameter and length), to accommodate applications in different sized and localized vessels. In one embodiment, the balloon is located near the tip of the catheter. In inflated condition, the balloon will fix the catheter in place in the targeted vessel, and prevent flow of fluid, delivered through a lumen exiting distal to the balloon, in the proximal direction (back along the catheter). (B) In another embodiment, the inflated balloon can restrict fluid delivery to the proximal region, where the fluid delivery lumen opens proximal to the balloon.

Figure 1A:
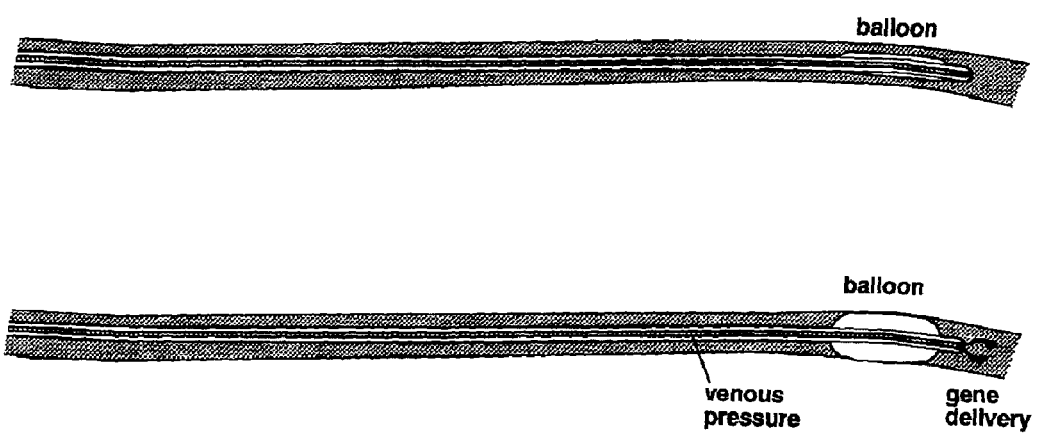
FIG. 1(A) Single balloon catheters for nucleic acid delivery
Figure 1B:
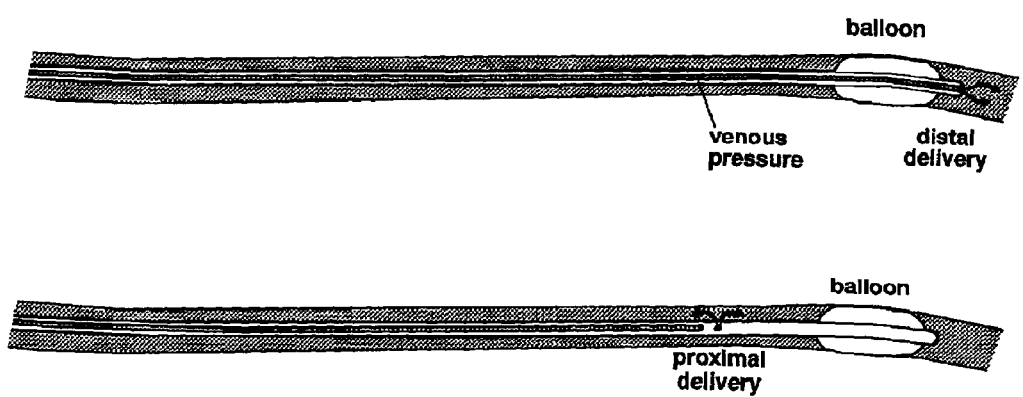
Figure 2:
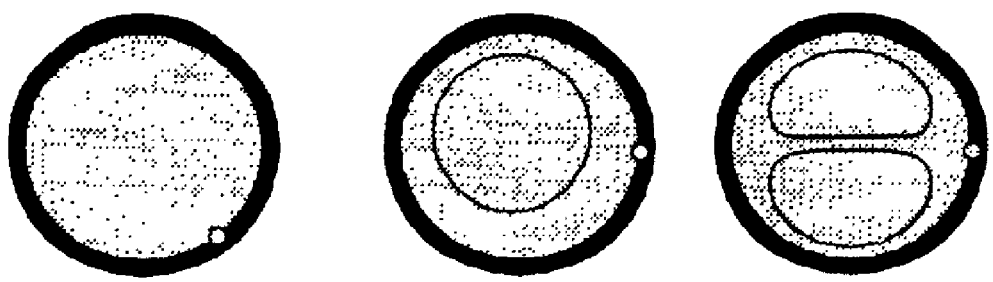

FIG. 2 Multilumen catheters for nucleic acid delivery

Catheters can be made with multiple lumens that can be accessed independently. For instance, catheters with 2, 3, or 4 lumens are diagrammed. The individual lumens can be of similar size, or of different size. In this diagram, catheters with unequal sized lumens are shown. Multiple lumen catheters can be used to perform several functions simultaneously. For instance, the three-lumen catheter cold be used to deliver a nucleic acid solution through the largest sized lumen, controlling a balloon through another lumen, and use the third lumen for real time pressure measurements (e.g., using a guidewire incorporating a pressure transducer).

Figure 3:
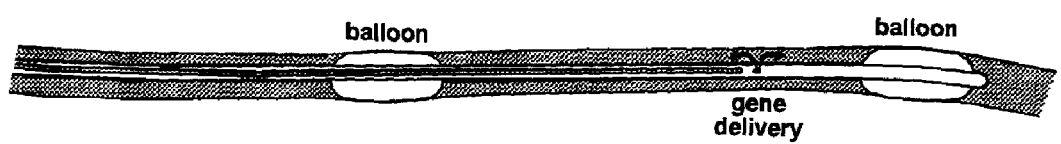

FIG. 3 Double balloon catheters for nucleic acid delivery

A double balloon catheter generally comprises a two-lumen catheter, in which one lumen is used to inflate or deflate the balloons and the other lumen for other purposes, e.g., guidewires, delivery of fluids, intravascular pressure measurements. The two balloons may also be operated independently, by including another lumen. Such catheters are available in many different sizes (diameter, length, distance between the two balloons), to accommodate applications in different sized and localized vessels. In one embodiment, one balloon is located near the tip of the catheter, the other balloon some distance proximal (e.g., 5 cm). In inflated condition, the two balloons will fix the catheter in place in the targeted vessel. Fluid (e.g., for nucleic acid delivery) can be delivered through a lumen exiting in the area between the two balloons. The inflated balloons prevent flow through the blood vessel outside the area enclosed by the two balloons. In another embodiment, the inflated balloons can restrict fluid delivery outside the region enclosed by the balloons.

Figure 4:
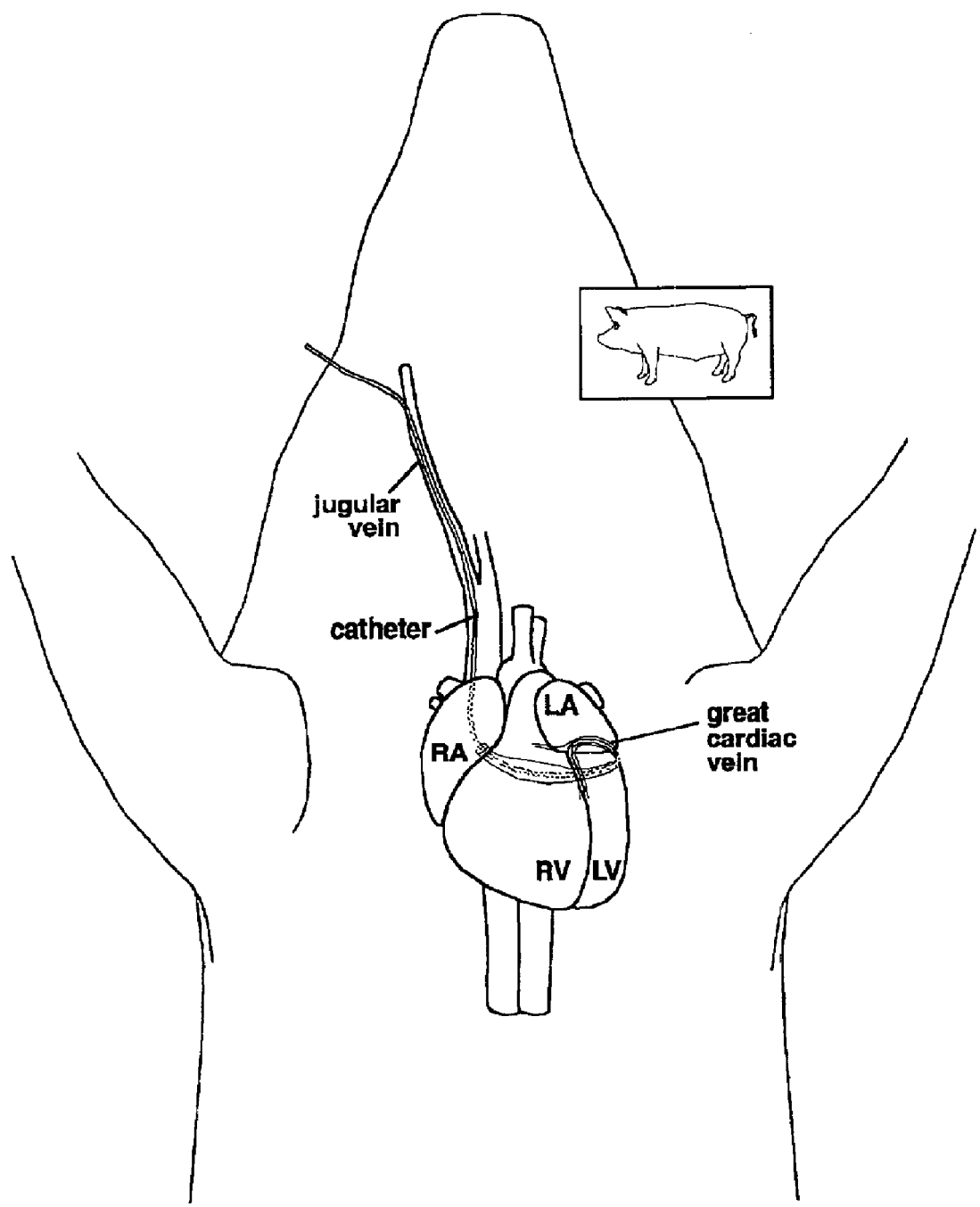

FIG. 4 Nucleic acid delivery to the heart

Nucleic acids are delivered to a specific region of the heart through a catheter. The catheter is advanced into the great cardiac vein via the jugular vein, superior vena cava, right atrium, and coronary sinus. Other areas of the heart can be targeted through other coronary veins (e.g., middle cardiac vein). Alternative nucleic acid routes include delivery through a catheter advanced into a coronary artery, or placement of a needle into a coronary vein or artery (e.g., during open heart surgery or using minimal invasive surgery).

DETAILED DESCRIPTION

Definitions

The term "nucleic acid" is a term of art that refers to a polymer containing at least two nucleotides. "Nucleotides" contain a sugar deoxyribose (in DNA) or ribose (in RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nucleic acid includes deoxyribonucleic acid ("DNA") and ribonucleic acid ("RNA"). DNA may be in the form of anti-sense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), antisense RNA, ribozymes, chimeric sequences, or derivatives of these groups. "Anti-sense" is a nucleic acid that interferes with the function of DNA and/or RNA. This may result in suppression of expression. Natural nucleic acids have a phosphate backbone, artificial nucleic acids may contain other types of backbones, nucleotides, or bases. These include PNAs (peptide nucleic acids), phosphothionates, and other variants of the phosphate backbone of native nucleic acids. In addition, DNA and RNA may be single, double, triple, or quadruple stranded. "Expression cassette" refers to a natural or recombinantly produced nucleic acid which is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The term "naked nucleic acids" indicates that the nucleic acids are not associated with a transfection reagent or other delivery vehicle that is required for the nucleic acid to be delivered to a target cell. A "transfection reagent" is a compound or compounds used in the prior art that bind(s) to or complex(es) with nucleic acids, and mediates their entry into cells. The transfection reagent also mediates the binding and internalization of nucleic acids into cells. Examples of transfection reagents include cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine are ineffective. Typically, the transfection reagent has a net positive charge that binds to the nucleic acid's negative charge. The transfection reagent mediates binding of nucleic acids to cells via its positive charge (that binds to the cell membrane's negative charge) or via ligands that bind to receptors in the cell. For example, cationic liposomes or polylysine complexes have net positive charges that enable them to bind to DNA or RNA.

Other vehicles are also used, in the prior art, to transfer genes into cells. These include complexing the nucleic acids on particles that are then accelerated into the cell. This is termed "biolistic" or "gun" techniques. Other methods include "electroporation" in which a device is used to give an electric charge to cells. The charge increases the permeability of the cell.

"Intravascular" refers to an intravascular route of administration that enables a polymer, oligonucleotide, or polynucleotide to be delivered to cells more evenly distributed and more efficiently than direct injections. Intravascular herein means within an internal tubular structure called a vessel that is connected to a tissue or organ within the body of an animal, including mammals. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein. "Intracoronay" refers to an intravascular route for delivery to the heart wherein the blood vessels are the coronary arteries and veins.

Delivery of a nucleic acid means to transfer a nucleic acid from a container outside a mammal to near or within the outer cell membrane of a cell in the mammal. The term "transfection" is used herein, in general, as a substitute for the term "delivery," or, more specifically, the transfer of a nucleic acid from directly outside a cell membrane to within the cell membrane. The transferred (or "transfected") nucleic acid may contain an expression cassette. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

"Protein" refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein (e.g., low density lipoprotein receptor). Therapeutic proteins that stay within the cell ("intracellular proteins") can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

"Vectors" are nucleic acids originating from a virus, a plasmid, or the cell of an organism into which another nucleic fragment of appropriate size can be integrated without loss of the vectors capacity for self-replication. Vectors introduce nucleic acids into host cells, where it can be reproduced. Examples are plasmids, cosmids, and yeast artificial chromosomes. Vectors are often recombinant molecules containing nucleic acid sequences from several sources. Vectors include viruses, for example adenovirus (an icosahedral (20-sided) virus that contains DNA; there are over 40 different adenovirus varieties, some of which cause respiratory disease), or retrovirus (any virus in the family *Retroviridae* that has RNA as its nucleic acid and uses the enzyme reverse transcriptase to copy its genome into the DNA and integrate into the host cell's chromosome).

"Afferent" blood vessels of organs are defined as vessels in which blood flows toward the organ or tissue under normal physiologic conditions. "Efferent" blood vessels are defined as vessels in which blood flows away from the organ or tissue under normal physiologic conditions. In the heart, afferent vessels are known as coronary arteries, while efferent vessels are referred to as coronary veins.

"Permeability" is defined herein as the propensity for macromolecules such as nucleic acids to move through vessel walls and enter the extravascular space. One measure of permeability is the rate at which macromolecules move through the vessel wall and out of the vessel. Another measure of permeability is the lack of force that resists the movement through the vessel wall and out of the vessel. Vessels contain elements that prevent macromolecules from leaving the intravascular space (internal cavity of the vessel). These elements include endothelial cells and connective material (e.g., collagen). High permeability indicates that there are fewer of these elements that can block the egress of macromolecules and that the spaces between these elements are larger and more numerous. In this context, high permeability enables a high percentage of nucleic acids being delivered to leave the intravascular space, while low permeability indicates that a low percentage of the nucleic acids will leave the intravascular space.

The permeability of a blood vessel can be increased by increasing the intravascular hydrostatic pressure. In a preferred embodiment, the intravascular hydrostatic pressure is increased by rapidly (from 1 seconds to 30 minutes) injecting a nucleic acid in solution into the blood vessel, which increases the hydrostatic pressure. In another preferred embodiment, hydrostatic pressure is increased by obstructing the outflow of the injection solution from the tissue for a period of time sufficient to allow delivery of a nucleic acid. Obstructing means to block or impede the outflow of injection fluid, thereby transiently (reversibly) blocking the outflow of the blood. Furthermore, rapid injection may be combined with obstructing the outflow in yet another preferred embodiment. For example, an afferent vessel supplying an organ is rapidly injected while the efferent vessel draining the tissue is blocked transiently (e.g., by ligation, or by an inflated intravascular balloon). The efferent vessel (also called the venous outflow or tract) draining outflow from the tissue is partially or totally clamped for a period of time sufficient to allow delivery of a nucleic acid. In the reverse, an efferent vessel is injected while the corresponding afferent vessel is occluded.

In another preferred embodiment, the intravascular pressure of a blood vessel is increased by increasing the osmotic pressure within the blood vessel. Typically, hypertonic solutions containing salts such as sodium chloride, sugars or polyols such as mannitol are used. "Hypertonic" means that the osmolality of the injection solution is greater than physiologic osmolality. "Isotonic" means that the osmolality of the injection solution is the same as the physiological osmolality (i.e., the tonicity or osmotic pressure of the solution is similar to that of blood). Hypertonic solutions have increased tonicity and osmotic pressure compared to the osmotic pressure of blood and cause cells to shrink.

The permeability of the blood vessel can also be increased by a biologically-active molecule such as a protein or a simple chemical such as histarine that increases the permeability of the vessel by causing a change in function, activity, or shape of cells within the vessel wall such as the endothelial or smooth muscle cells. Typically, biologically active molecules that affect permeability interact with a specific receptor or enzyme or protein within the vascular cell to change the vessel's permeability. Biologically active molecules include vascular permeability factor (VPF) which is also known as vascular endothelial growth factor (VEGF). Another type of biologically active molecule can also increase permeability by changing the extracellular connective material. For example, an enzyme could digest the extracellular material and increase the number and size of the holes of the connective material. Other biologically active molecules that may alter the permeability include calcium channel blockers (e.g., verapamil, nicardipine, diltiazem), beta-blockers (e.g., lisinopril), phorbol esters (e.g., PKC), ethylenediaminetetraacetic acid (EDTA), adenosine, papaverine, atropine, and nifedipine.

Delivery of nucleic acids

A minimally invasive and clinically viable in vivo delivery system of naked nucleic acids, nucleic acids combined with transfection reagents, plasmid DNA, or viruses to a heart is described in this specification. The intravascular delivery of nucleic acids into coronary vessels results in high levels of reporter gene expression in pig heart muscle. A retrograde transvenous approach along with an arterial route can be used to deliver nucleic acids expressing therapeutically relevant proteins to myocardial beds supplied by occluded coronary arteries.

The delivery of naked DNA to the heart is described in one preferred embodiment using direct injections into coronary arteries and veins. In another preferred embodiment, percutaneous transluminal coronary angioplasty (PTCA) catheters are advanced into the coronary venous system from a peripheral vein. In a preferred embodiment, double lumen balloon catheters are positioned into coronary veins from peripheral vessels in pigs and plasmid DNA solutions are injected under pressure to transfect cardiac muscle cells. In another preferred embodiment, an injection system is described that allows for automated regulation of injection speed and volume correlated to the pressure in the injected vessel. Coronary angioplasty catheters are used to simultaneous inject fluids into the selected coronary bed and measure the intracoronary venous hydrostatic pressure during and after injection.

Reporter gene expression is optimized and toxicity (tissue damage) is minimized by varying the volume of the plasmid DNA solution and the speed of injection; varying the osmotic pressure by the addition of mannitol to the injection solution; increasing fluid and plasmid DNA extravasation, e.g., by vessel dilation using papaverine or VEGF protein pre-injection; performing safety assessment via routine histologic studies and measurements of serum CPK and troponin.

Efficient gene transfer into cardiac muscle cells was obtained following injection of plasmid DNA solutions into coronary arteries and veins in pig hearts. Luciferase reporter genes were used to assess total foreign gene expression in the heart tissue and the reporter gene LacZ (expressing β-galactosidase) to determine the percentage and type of cells that express plasmid DNA at several time points following injection. Similar high levels of expression were measured following catheter-based plasmid DNA delivery. This suggests that the treatment of myocardial ischemia in patients with coronary artery disease using this method is feasible. An advantage of this method over direct interstitial injection of plasmid DNA into the heart is that a complete (ischemic) bed can be targeted. Direct interstitial injection results in very localized gene transfer and expression. In contrast, intravascular delivery of plasmid DNA can result in more widespread cardiac gene expression.

There are three types of reporter (marker) gene products that are expressed from reporter genes. The reporter gene/protein systems include:

a) Intracellular gene products such as luciferase, β-galactosidase, or chloramphenicol acetyl transferase. Typically, they are enzymes whose enzymatic activity can be easily measured.

b) Intracellular gene products such as β-galactosidase or green fluorescent protein which identify cells expressing the reporter gene. On the basis of the intensity of cellular staining, these reporter gene products also yield qualitative information concerning the amount of foreign protein produced per cell.

c) Secreted gene products such as growth hormone, factor IX or alpha1-antitrypsin are useful for determining the amount of a secreted protein that a gene transfer procedure can produce. The reporter gene product can be assayed in a small amount of blood.

We have disclosed gene expression achieved from reporter genes in specific tissues. The terms "therapeutic" and "therapeutic results" are defined in this application as levels of gene products, including reporter (marker) gene products, which indicate a reasonable expectation of gene expression using similar compounds (nucleic acids), at levels considered sufficient by a person having ordinary skill in the art of gene therapy. For example: Hemophilia A and B are caused by deficiencies of the X-linked clotting factors VIII and IX, respectively. Their clinical course is greatly influenced by the percentage of normal serum levels of factor VIII or IX: <2%, severe; 2–5%, moderate, and 5–30% mild. This indicates that in severe patients only 2% of the normal level can be considered therapeutic. Levels greater than 6% prevent spontaneous bleeds but not those secondary to surgery or injury. A person having ordinary skill in the art of gene therapy would reasonably anticipate therapeutic levels of expression of a gene specific for a disease based upon sufficient levels of marker gene results. In the Hemophilia example, if marker genes were expressed to yield a protein at a level comparable in volume to 2% of the normal level of factor VIII, it can be reasonably expected that the gene coding for factor VIII would also be expressed at similar levels.

EXAMPLES

The following examples are intended to illustrate, but not limit, the present invention.

Example 1

In vivo luciferase expression from naked plasmid DNA transfected to a pig heart

Solutions of pCI-Luc$^+$ were injected into coronary arteries and veins in pig heart. pCI-Luc$^+$ is a plasmid DNA expression vector in which an optimized version of the firefly luciferase gene (Promega, Madison, Wis.) is expressed under transcriptional control of the CMV promoter (basic expression vector is pCI, Promega, Madison, Wis.). The hearts of 30–40 kg domestic pigs were accessed via a limited left thoracotomy through the fifth intercostal space. A 27-gauge needle was inserted into a left anterior descending (LAD, great cardiac) or right posterior descending (middle cardiac) vein or artery, and ligated in place. The ligation serves to keep the needle in place and to direct flow distal from the needle. The corresponding artery or vein was transiently occluded during the injection. A pre-injection into the coronary artery or vein of 6 ml papaverine solution (0.5 mg/ml) was given in 15–20 seconds. After 5 minutes, a solution of 50 $\mu$g/ml plasmid DNA in saline with 15% mannitol (w/v) was injected in ~20–30 seconds. Following injection, the ligation and needle were removed, bleeding stopped, and the pericardium and chest closed. In most pigs, the LAD bed and a site in the circumflex were injected. In two pigs, also direct interstitial injections were performed for comparison.

Two days following injection, the animals were sacrificed and sections from the injection site were excised and assayed for reporter gene expression. Sections from the heart (ca. 1.5 gram each) were homogenized in a Triton X-100 lysis buffer. Luciferase activity was measured with an Analytical Luminescence Laboratories luminometer. Activity levels are expressed as the amount of luciferase protein per gram of heart tissue. Plasmid DNA was obtained from BayouBioLabs (Harahan, La.) and was supercoiled purified and endotoxin free.

Luciferase expression in the area around the injection site averaged 26.2 ng/g tissue (range 2.3–61.8; n=5). Both arterial and venous delivery resulted in efficient luciferase expression. In one animal, we compared intravenous delivery while transiently occluding the corresponding artery with leaving arterial flow open. Luciferase expression levels were 7.22 vs. 7.76 ng/g, respectively. This suggests that the capillary bed itself accounts for sufficient resistance to retrograde flow to increase vascular permeability above the required threshold for efficient plasmid DNA extravasation.

Direct interstitial injection of 500 $\mu$g plasmid DNA in 500 $\mu$l saline resulted in an average expression level of 70.3 ng luciferase per gram tissue (range 9.6–115.2; n=3). Expression appeared far more limited to the area of injection. Analysis of tissues around the injected bed after intravascular delivery, showed lower levels of expression extending to relatively distant sites.

Example 2

Estimation of the number of transfected cardiomyocytes following plasmid DNA delivery into a cardiac vein Intravenous injection of pCI-LacZ was performed to determine the cell type and extent of transfection. Crysosections (10 $\mu$m) were stained for $\beta$-galactosidase expression as described before. A low percentage of transfected cardiomyocytes was detected two days following injection. No endothelial cells were found to express $\beta$-galactosidase. The percentage of $\beta$-galactosidase positive cells appears rather low for the amount of luciferase expression that was found in the same tissue samples (15 ng/g, generated by ~10-fold less pCI-Luc$^+$ than was used in the experiments describe in example 1; in this experiment, pCI-Luc$^+$ was co-injected with pCI-LacZ at a ratio of 1:9). The same tissue sections were also stained with hematoxyline-osin. No gross abnormalities were observed.

Example 3

Plasmid DNA Delivery to Coronary Veins Via a Catheter

Gene transfer experiments were performed in 30–50 kg Yorkshire domestic swine (Sus scrofa). The pigs were sedated with telezol (20–30 mg IM), induced with pentobarbitol (250–500 mg IV), and endotracheally intubated. Anesthesia was maintained with inhaled isoflurane (0.5–3%). The right carotid artery and internal jugular vein were exposed by surgical cutdown and coronary angiography was performed. Heparin (100 U/kg, IV) was administered. A 10 Fr guiding catheter was advanced to the coronary sinus, and a 7 Fr balloon-tipped triple lumen catheter was advanced over a 0.014 inch guidewire into the cardiac vein draining the left anterior descending (great cardiac vein) or right posterior descending (middle cardiac vein) territories. Low pressure injections of diluted iodinated contrast were used, in conjunction with the coronary angiogram, to delineate the myocardial territory drained by each vein.

The larger lumen of the balloon-tipped triple lumen catheter is used for fluid injection, while the smaller lumen is used to monitor cardiac vein pressures during plasmid DNA infusion; the third lumen is used to inflate and deflate the balloon. Following placement of the catheter, the balloon was inflated, and 6 ml saline or 6 ml saline with 3 mg papaverine was instilled through the large lumen (which opens distal to the balloon). The installation required 3–20 seconds and resulted in slightly increased venous pressure (10–350 mmHg). After 5 minutes, the balloon was deflated for 20–30 seconds and then inflated again followed by plasmid DNA delivery. A saline solution containing 100 $\mu$g/ml pCI-Luc$^+$ was rapidly delivered through the main lumen. During the injections of 25–30 ml plasmid DNA solution in 8–20 seconds, the intravenous pressure increased (120–500 mmHg). In some pigs, two sites were injected (one in the posterior descending, the other in the left anterior descending territory); in other pigs, only one site was injected (left anterior descending).

Two days following injection, the animals were sacrificed, the heart excised, divided in 1–2 gram sections, and assayed for reporter gene expression. Maximum expression levels (near the site of plasmid DNA delivery) varied from 1.4 to 456.9 ng luciferase per gram of heart tissue (n=8).

Example 4
A porcine model of chronic myocardial ischemia

A well characterized porcine model of chronic myocardial ischemia is utilized. This model involves placement of an ameroid constrictor around the proximal left circumflex coronary artery, which results in the gradual stenosis and occlusion of the artery approximately 10 days after placement. Collateral blood vessels partially revascularize the occluded vascular bed so that minimal necrosis is apparent and myocardial blood flow and regional contractile function at rest is normal. However, increased myocardial oxygen demands induced by rapid pacing or synthetic catecholamine infusion results in myocardial ischemia in the circumflex territory, as evidenced by regional wall motion abnormalities and attenuated augmentation of myocardial blood flow. Previous studies have demonstrated that collateral vessel development is complete within 21 days, and remains unchanged for up to 4 months.

Two pigs were instrumented with proximal left circumflex ameroid constrictors and demonstrated stress-induced myocardial ischemia. Three to four weeks after aneroid placement, cardiac catheterization and coronary angiography demonstrated complete occlusion of the proximal left circumflex coronary artery within the surgically implanted constrictor. Short-axis two dimensional and M-mode echocardiograms were obtained at the level of the heads of the papillary muscles in the lightly anesthetized pigs. At resting heart rates, the fractional thickening of the posterolateral wall of the left ventricle was normal (33%). During rapid atrial pacing at 200 beats/min, posterolateral wall fractional thickening was significantly impaired (11%), consistent with myocardial ischemia in the vascular bed of the left circumflex coronary artery.

Example 5
Modified catheter

A 10F guide catheter was shortened to 50–60 cm (from 100 cm). The bend was adjusted as needed. The injection catheter is shortened to 80–90 cm down from 135 cm. A 2 cm portion of the tip end was shaved by 0.005–0.009 inch to accommodate the thin walled silastic balloon that is fabricated on the narrowed portion. A fluid-filled catheter was inserted in the large lumen to measure the infusion pressure.

Example 6
Modified two-lumen catheter

A custom, double-lumen balloon angioplasty catheter and an angioplasty guidewire with micro-miniaturized piezo pressure-transducer elements to measure venous bed pressures during injections, can be used as a more practical and convenient alternative.

Example 7
Modified three-lumen catheter

A triple-lumen balloon angioplasty catheter can be used to accommodate nucleic acid delivery, control of balloon, and a fluid-filled lumen for pressure measurements.

Example 8
Automated injection system

An automated injection system is constructed to provide reproducible and consistent delivery of nucleic acid solutions. The system consists of a Macintosh PowerBook G3 laptop computer (Apple Computer, Cupertino, Calif.), a DAQCard AI-16E-4 data acquisition input and output system (National Instruments, Austin, Tex.), and LabView software (National Instruments). The intravenous pressure (distal to the inflated balloon catheter) is measured, using a pressure transducer guidewire or a fluid-filled lumen attached to a pressure transducer. The pressure transducer is coupled to the DAQCard, the signal digitized and read into the custom control program (made in LabView). The pressure reading is compared to a preset target value. The control program can directly influence the speed of injection of the power injector. A pressure value below the preset would result in an increase in the injection rate; a pressure value above the preset would result in a decrease in the injection rate. The control software allows for regulation of maximum increases/decreases in injection rate in order to prevent extremely fast ramping or oscillations. It also allows for control of maximum injection volume. In another embodiment, the system will also measure other clinical relevant parameters (heart rate, oxygen saturation level, breathing/ventilation rate, etc.), as to provide information on these procedure related variables.

The foregoing examples are considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering nucleic acids to muscle cells in a mammalian heart, comprising: a) accessing an in vivo blood vessel; and, b) inserting an injector into the blood vessel near or in the heart, in vivo, and injecting a solution containing nucleic acids into the blood vessel lumen and increasing hydrostatic pressure in the lumen thereby delivering the nucleic acids to the heart muscle cells outside of the blood vessel via the pressure, wherein invasiveness is limited to accessing the blood vessel, inserting the injector into the blood vessel, and injecting the solution.

2. The process of claim 1 wherein the nucleic acid is expressed.

3. The process of claim 2 wherein injecting the nucleic acid includes injecting the nucleic acid through a catheter.

4. The process of claim 3 wherein injecting the nucleic acid includes injecting a predetermined volume of nucleic acid during a predetermined time.

5. The process of claim 1 wherein the nucleic acid is selected from the group consisting of DNA, RNA, plasmid DNA, oligonucleotides, and nucleic acid contained in viruses.

6. The process of claim 1 wherein the nucleic acid consists of naked DNA.

7. A process for gene expression in mammalian heart muscle cells, comprising: a) accessing an in vivo blood vessel; b) inserting an injector into the blood vessel near or in the heart, in vivo, and injecting a solution containing nucleic acids encoding a protein into the blood vessel lumen and increasing hydrostatic pressure in the lumen thereby delivering the nucleic acids to the heart muscle cells outside of the blood vessel via the pressure; and, expressing the nucleic acids to provide a therapeutic protein, wherein invasiveness is limited to accessing the blood vessel, inserting the injector into the blood vessel, and injecting the solution.

8. The process of claim 7 wherein the nucleic acid is selected from the group consisting of DNA, RNA, plasmid DNA, and nucleic acid contained in viruses.

9. The process of claim 7 wherein injecting the nucleic acid includes injecting the nucleic acid through a catheter.

10. The process of claim 7 wherein the nucleic acid consists of naked DNA.

* * * * *